(12) United States Patent
Konstorum

(10) Patent No.: US 8,864,656 B2
(45) Date of Patent: Oct. 21, 2014

(54) ENDOSCOPE COMBINED DEFLECTION CONTROL AND LOCK

(71) Applicant: Gyrus ACMI, Inc., Southborough, MA (US)

(72) Inventor: Gregory S. Konstorum, Stamford, CT (US)

(73) Assignee: Gyrus Acmi, Inc., Southborough, MA (US)

( * ) Notice: Subject to any disclaimer, the term of this patent is extended or adjusted under 35 U.S.C. 154(b) by 47 days.

(21) Appl. No.: 13/746,683

(22) Filed: Jan. 22, 2013

(65) Prior Publication Data

US 2013/0144125 A1    Jun. 6, 2013

Related U.S. Application Data

(63) Continuation-in-part of application No. 12/455,593, filed on Jun. 3, 2009, now Pat. No. 8,366,604.

(51) Int. Cl.

| | |
|---|---|
| *A61B 1/00* | (2006.01) |
| *A61B 1/018* | (2006.01) |
| *A61B 1/303* | (2006.01) |
| *A61B 1/005* | (2006.01) |
| *A61B 1/04* | (2006.01) |
| *A61B 1/12* | (2006.01) |
| *A61B 1/06* | (2006.01) |

(52) U.S. Cl.
CPC ............... *A61B 1/0055* (2013.01); *A61B 1/018* (2013.01); *A61B 1/00117* (2013.01); *A61B 1/0676* (2013.01); *A61B 1/303* (2013.01); *A61B 1/0057* (2013.01); *A61B 1/04* (2013.01); *A61B 1/0011* (2013.01); *A61B 1/12* (2013.01); *A61B 1/00066* (2013.01); *A61B 1/0684* (2013.01); *A61B 1/0052* (2013.01); *A61B 1/00121* (2013.01); *A61B 1/0008* (2013.01)
USPC ........... 600/131; 600/125; 600/139; 600/146; 600/148

(58) Field of Classification Search
USPC ........... 600/125, 131, 139–152; 604/523–528
See application file for complete search history.

(56) References Cited

U.S. PATENT DOCUMENTS

| | | | |
|---|---|---|---|
| 6,749,560 B1 | 6/2004 | Konstorum et al. | |
| 6,780,151 B2 | 8/2004 | Grabover et al. | |

(Continued)

FOREIGN PATENT DOCUMENTS

| | | | |
|---|---|---|---|
| EP | 0306723 A1 | 3/1989 | |
| EP | 1832224 A1 | 9/2007 | |

(Continued)

*Primary Examiner* — Matthew J Kasztejna
*Assistant Examiner* — Kevin G Barry, III
(74) *Attorney, Agent, or Firm* — Harrington & Smith

(57) ABSTRACT

An endoscope including a shaft having a deflectable distal end; a main section at a proximal end of the shaft, where the main section forms a handle of the endoscope; and a deflection control connected to the distal end. The deflection control includes a combined lock and deflection control member at the main section comprising a control lever pivotably connected to the main section at a pivot and extending away from the pivot in a general cantilever fashion, and a lock lever pivotably connected to the control lever. A first end of the lock lever is configured to contact the main section. A second end of the lock lever is configured to be pressed inward on the control lever towards the main section to pivot the first end out of contact with the main section.

15 Claims, 7 Drawing Sheets

(56) References Cited

U.S. PATENT DOCUMENTS

| | | |
|---|---|---|
| 2001/0037051 A1 | 11/2001 | Fujii et al. |
| 2004/0193016 A1 | 9/2004 | Root et al. .................... 600/146 |
| 2007/0203474 A1* | 8/2007 | Ryan et al. .................... 604/528 |
| 2007/0219411 A1 | 9/2007 | Dejima et al. |
| 2009/0054733 A1* | 2/2009 | Marescaux et al. ........... 600/141 |
| 2012/0078050 A1 | 3/2012 | Schwartz et al. |

FOREIGN PATENT DOCUMENTS

| | | |
|---|---|---|
| EP | 2106751 A1 | 10/2009 |
| EP | 2123211 A1 | 11/2009 |
| WO | WO-02/089891 A2 | 11/2002 |
| WO | WO-2007/081706 A2 | 7/2007 |
| WO | WO 2008/045374 A2 | 4/2008 |
| WO | WO-2008/045374 A2 | 4/2008 |

* cited by examiner

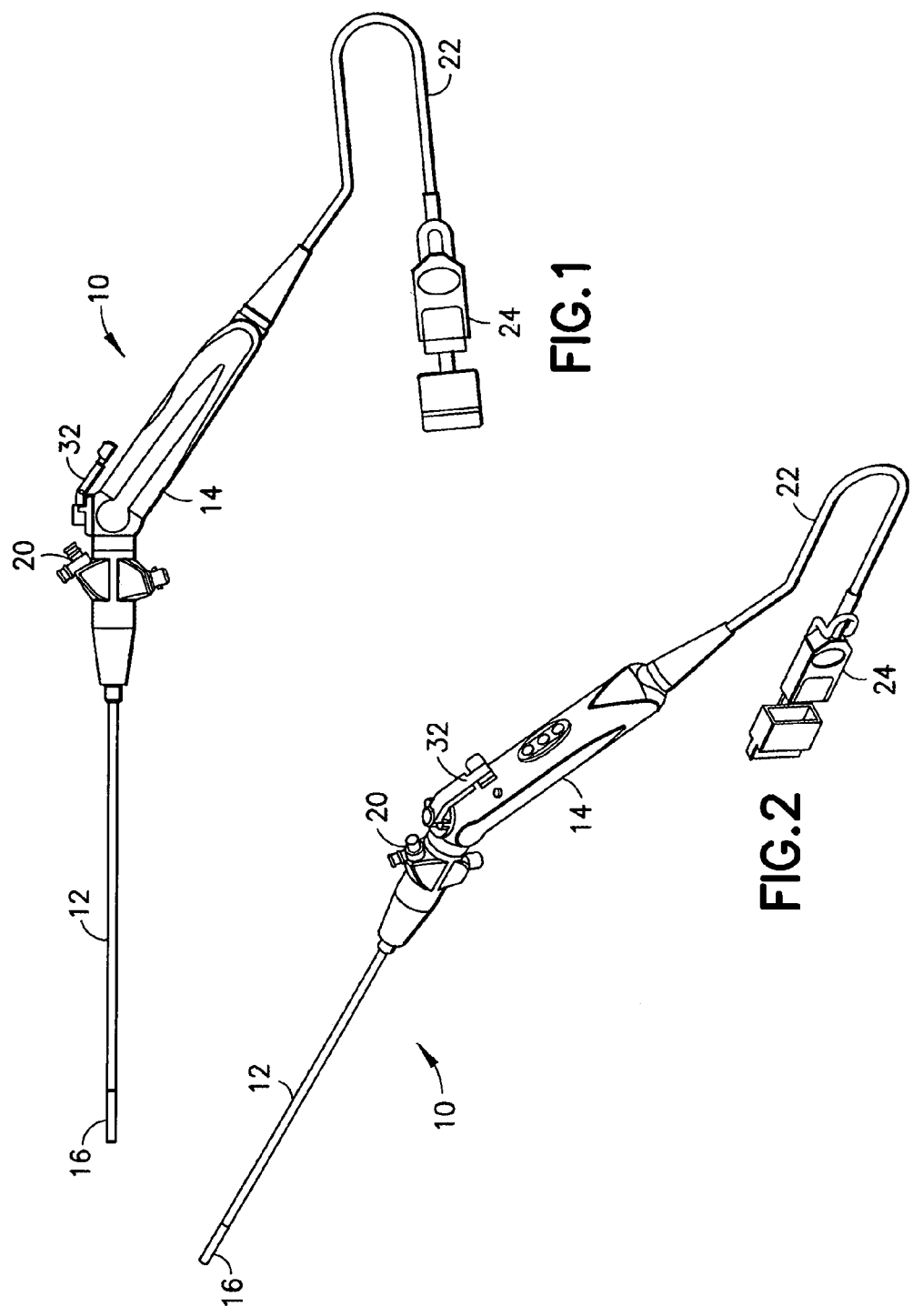

ENDOSCOPE COMBINED DEFLECTION CONTROL AND LOCK

CROSS REFERENCE TO RELATED APPLICATION

This is a continuation-in-part application of copending application Ser. No. 12/455,593 filed Jun. 3, 2009 which is hereby incorporated by reference in its entirety.

BACKGROUND OF THE INVENTION

1. Field of the Invention

The invention relates to an endoscope and, more particularly, to a combined deflection control and lock.

2. Brief Description of Prior Developments

There are flexible endoscopes with steering distal tip control mechanisms with separate deflection control and lock (or brake) levers. A disadvantage of this construction is that operation of a deflection control and a separate lock or brake requires using two hands or fingers, or using one finger with at least two steps (a lock/unlock step and a deflection step). For example, U.S. Pat. No. 6,780,151 B2, which is hereby incorporated by reference in its entirety, discloses an endoscope with a control lever 17 and a separate brake lever 22. After the control lever 17 is moved by a finger, such as a thumb, the brake 22 can be moved by the same finger or a finger of another hand.

There is a desire to provide an endoscope deflection control and lock which can be operated by a single finger of a user.

SUMMARY

The following summary is merely intended to be exemplary. The summary is not intended to limit the scope of the claimed invention.

In accordance with one aspect of the invention, an endoscope is provided including a shaft having a deflectable distal end; a main section at a proximal end of the shaft, where the main section forms a handle of the endoscope; and a deflection control connected to the distal end. The deflection control includes a combined lock and deflection control member at the main section comprising a control lever pivotably connected to the main section at a pivot and extending away from the pivot in a general cantilever fashion, and a lock lever pivotably connected to the control lever. A first end of the lock lever is configured to contact the main section. A second end of the lock lever is configured to be pressed inward on the control lever towards the main section to pivot the first end out of contact with the main section.

In accordance with another aspect of the invention, an endoscope is provided comprising a shaft having a deflectable distal end; a handle at a proximal end of the shaft; and a deflection control connected to the distal end, wherein the deflection control comprises a control lever pivotably connected to a first side of the handle, where the control lever extends from the first side of the handle in a general cantilever fashion, over an adjacent second side of the handle; and a lock lever pivotably connected to the control lever, wherein the lock lever comprises a lock section adapted to contact a lock section on the handle.

In accordance with another aspect of the invention, a method comprises pivotably connecting a control lever to a handle section of an endoscope, where the control lever is connected to a control wire pulley of a deflection control system of the endoscope, where the control lever is adapted to be rotated on the handle section to rotate the pulley; and pivotably connecting a lock lever to the control lever, where the lock lever is adapted to pivot on the control lever between a locked position and an unlocked position, where in the locked position a locking section on a first end of the lock lever engages a lock section of the handle section, and where in the unlocked position the locking section on the first end of the lock lever does not engage the lock section of the handle section.

In accordance with another aspect of the invention, a method is provided comprising rotating a lock lever in a first direction from a first locked position to a second unlocked position, where the lock lever is pivotably connected to a control lever, where the control lever is pivotably connected to a control wire pulley of a deflection control system of the endoscope; and after the lock lever is moved to the second unlocked position, moving the lock lever and the control lever together in a second different direction to thereby rotate the control wire pulley.

BRIEF DESCRIPTION OF THE DRAWINGS

The foregoing aspects and other features of the invention are explained in the following description, taken in connection with the accompanying drawings, wherein:

FIG. 1 is a side view of an endoscope comprising features of the invention;

FIG. 2 is a perspective view of the endoscope shown in FIG. 1;

DETAILED DESCRIPTION OF EMBODIMENTS

Figure 3:
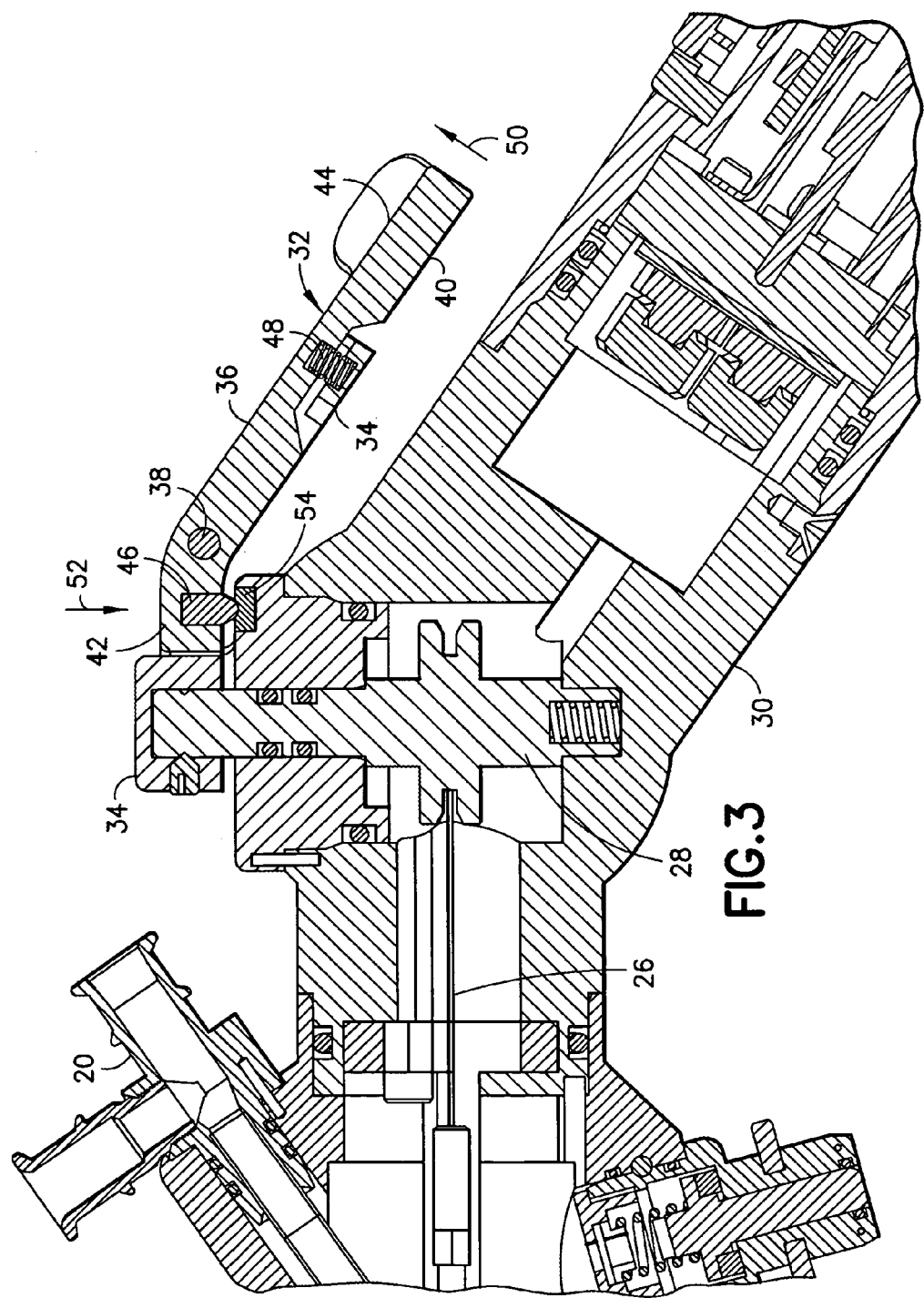
FIG. 3 is an enlarged cross sectional view of a portion of the endoscope shown in FIGS. 1-2.

Referring to FIGS. 1 and 2, an endoscope 10 is shown incorporating features of the invention. Although the invention will be described with reference to the example embodiments shown in the drawings, it should be understood that the invention can be embodied in many alternate forms of embodiments. In addition, any suitable size, shape or type of elements or materials could be used.

The endoscope 10, in this embodiment, is a hysteroscope used for inspection of the uterine cavity of a patient. The hysteroscope is an optical instrument connected to a video unit, and comprises channels for delivery and removal of a distention medium and a tool. However, features of the invention could be used in any suitable type of endoscope. In the example shown, the endoscope comprises a shaft 12 and a main section 14 which forms a handle. The shaft 12 has a front or distal, end 16 which is controllably deflectable. In this embodiment the rest of the shaft is substantially rigid. The distal end 16 is adapted to deflection in left and right directions. However, any suitable deflection capability could be provided.

Figure 4:
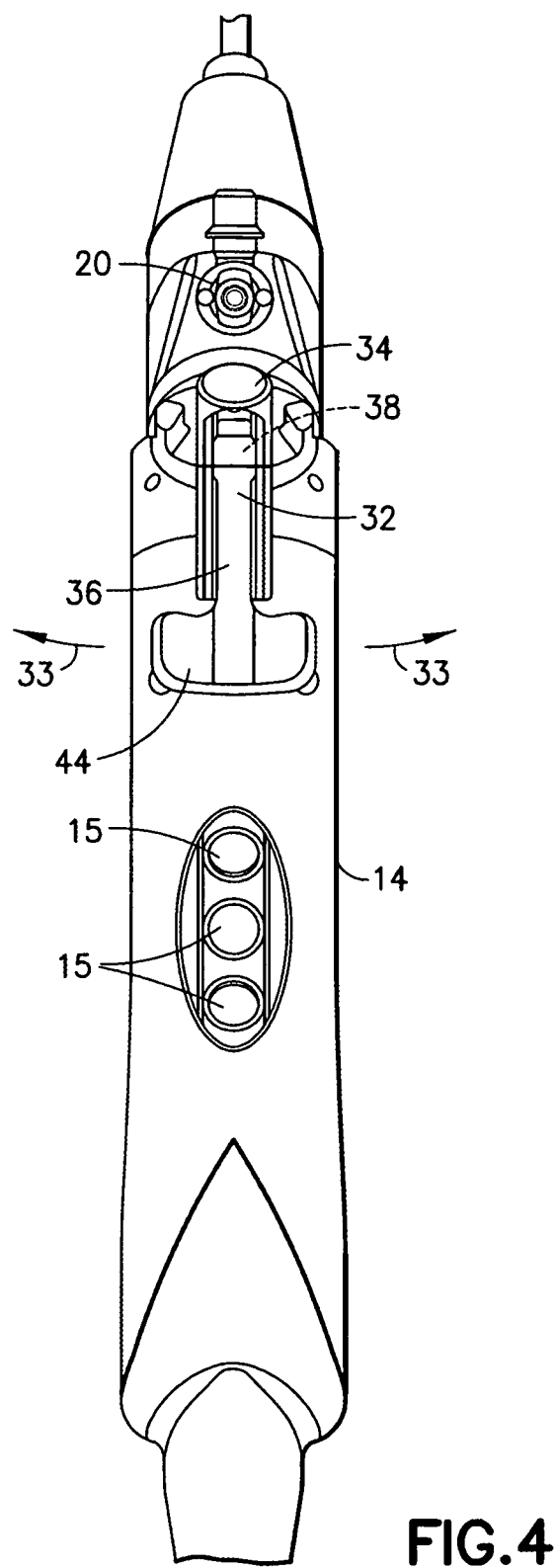
FIG. 4 is a top plan view of a portion of the endoscope shown in FIGS. 1-2.

The main section 14 is located at the proximal end of the shaft 12. Referring also to FIG. 3, she main section 14 has a working instrument/irrigation inlet 20, and a cable 22 with a connector 24 adapted to be connected to another device. An electrical cable extends from light emitting diodes (LEDs) in the distal end 16 to the main section 14. Alternatively, an optical cable for illuminating in front of the distal end 16 could be provided. Deflection control wires or cables 26 extend from the distal 6 to a pulley 28 in the main section 14. The pulley 28 is rotatably mounted in the frame 30 of the main section 14. As seen in FIG. 4, in this embodiment the main section 14 has buttons 15 to control features of another device which the connector 24 is connected to.

The pulley 28 and wires 26 form part of a deflection control for a user to control deflection of the deflectable distal end 16 from the main section 14. The deflection control also comprises a lever assembly 32. The lever assembly 32 is connected to the pulley 28 to axially rotate the pulley 28 when the lever assembly 32 is rotated right or left as indicated by arrows 33 in FIG. 4. The lever assembly 32 comprises a first lever 34 and a second lever 36. The first lever 34 is fixedly connected to the pulley 28. The second lever 36 is pivotably connected to the first lever 34 by a pivot pin 38. Thus, the second lever 36 can pivot on the first lever 34, and the second lever 36 is connected to the pulley 28 by the first lever 34; in series. However, any suitable movable connection of the second lever on the first lever could be provided.

The second lever 36 has a first end 40 and a second end 42 on opposite sides of the pivot pin 33. Referring also to FIG. 3, the first end 40 forms a finger receiver area 44 sized and shaped to receive a finger of a user, such as a thumb. The second end 42 has a lock/brake 46. In this embodiment the lock/brake 16 is a pin attached to the second end 42. However, any suitable lock/brake could be provided. A spring 48 is provided between the first and second levers 34, 36 to bias the second end 42 upward (see arrow 50) and the first end 40 downward (see arrow 52) on the first lever 34. However, a user can use his/her thumb to depress the first end 40 (reverse to direction 50) to thereby pivot the second lever 36 at the pivot pin 38 and move the second end 42 upward (reverse to direction 52).

The main section 14 includes a lock pad 54 located opposite the lock/brake 46. In this embodiment the pad 54 is an insert which is fixedly inserted into a receiving area of the main section. The insert has a general curved or arched shape. However, in an alternate embodiment the lock pad could be integrally formed with the frame of the main section, or any suitably sized and shaped lock/brake section (for engaging with the lock/brake 46 of the lever assembly) could be provided.

Figure 5:
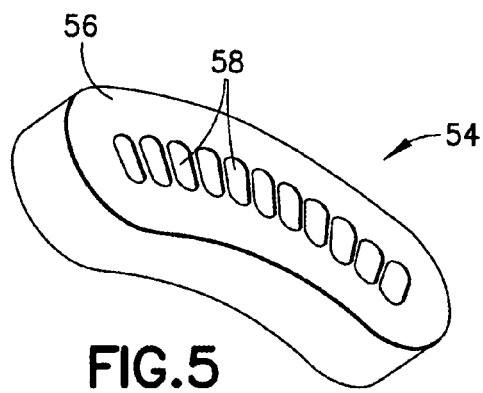
FIG. 5 is a perspective view of the lock/brake pad shown in FIG. 3.
Figure 6:
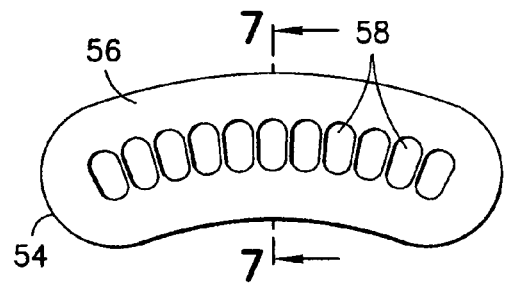
FIG. 6 is a top plan view of the pad shown in FIG. 5.
Figure 7:
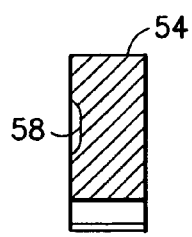
FIG. 7 is a cross sectional view of the pad shown in FIG. 6 taken along line 7-7.

Referring also to FIGS. 5-7, the pad 54 comprises a top side 56 having a series of recesses 58. The recesses 58 are sized, shaped and arranged in an arch or curve to receive the bottom tip of the pin 46 at different angular positions of the lever assembly 32. The recesses 58 allow positive location of the pin 46, and, thus, positive location of the angular position of the lever assembly 32, at one of a plurality of fixed predetermined locations selected by the user. When the second lever 36 is at its home position (with the second end 42 biased downward by the spring 48), the pin 46 is biased into one of the recesses 58. This prevents the lever assembly 32 from rotating relative to the main section 14 and, thus, prevents the lever assembly 32 from rotating the pulley 28, This forms a lock or brake for the deflection control system; fixing the position or shape of the distal end 16 on the shaft 12. The pin 46 forms a first lock/brake section which engages with a second lock/brake section formed by the pad 54.

With the same hand holding the handle formed by the main section 14, the user can use his or her thumb to depress the first end 40 of the second lever 36 (in a direction reverse to direction 50) to thereby disengage the pin 46 from the lock pad 54. The user is then free to swing the lever assembly 32 (both levers 34, 36 moving together in unison) left or right as indicated by arrows 33. Once a desired deflection of the distal end 16 is obtained, the user can release the first end 40 of the second lever 36 and the spring 48 can automatically biased the second lever 36 back to its home position. This automatically locks the lever assembly at a fixed angular position on the main section 14 due to the re-engagement of the lock/brake sections 46, 54.

With the invention, a construction can be provided which has an integrated deflection control and lock (brake) lever with an ergonomic design, and the lever can be activated with one finger (by a left of right hand person) eliminating the need of using two hands or fingers, or using two steps with a single finger.

With the example embodiment of the invention described above, the control lever 34 is firmly attached, such as with screws, to the external part of a pulley or pull cable mechanism 28. The lock (brake) lever 36 is pivotably attached to the control lever 34. A pin lock 46 is attached to one side of the lock lever, and a compression spring is placed between both levers at the other side of the lock lever; with the pivot pin in between. The lock insert 54 is placed and secured to the top surface of the endoscope enclosure/housing. The insert can be made from different materials and configurations.

Due to the location of the lock pin, the compression spring and the pivot pin, the lock pin creates a compression force to the lock pad/insert and the control lever is locked. In the example construction, the combined lever is always in the lock mode until positively moved by the user. In order to deflect the distal end 16 of the endoscope, the proximal end of the lock lever is pushed down first with a thumb (for the shown embodiment) to disengage the lock pin from the lock pad. Then, the combined lever assembly can be rotated with the thumb to the right or left causing the distal tip to deflect accordingly; dependent on the way the pull cables or wires attached to the pulley.

Figure 8:
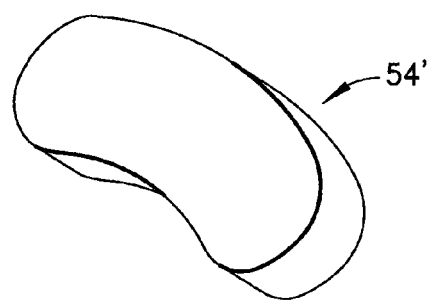
FIG. 8 is a perspective view of an alternate embodiment of the pad shown in FIGS. 5-7.
Figure 9:
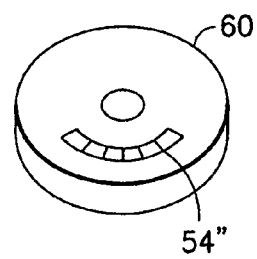
FIG. 9 is a perspective view of an alternate embodiment of the frame piece shown in FIG. 3 showing an integrally formed lock/brake pad.

The lock pad insert can be made from rubber with brake action or from metal with indents with clicking action or holes for lock action. Referring also to FIG. 8, an alternate embodiment of the main section's lock pad 54' is shown without recesses, such as when the pad is made of rubber. Referring also to FIG. 9, an alternate embodiment is shown where the lock pad 54" is made of metal integral with the frame piece 60. The pin 46 is preferably metal, but could be made of rubber or polymer material or could be integrally formed with the second lever.

A method of manufacturing an endoscope can be provided comprising:
  connecting a first lever to a control wire pulley of a deflection control system of the endoscope, wherein the lever is adapted to be rotated to rotate the pulley; and
  connecting a second lever to the first lever, wherein the second lever is adapted to pivot on the first lever.

The method can further comprise locating a spring between the first and second levers to bias the second lever towards a locked position. The method can further comprise biasing a lock section of the second lever against a lock section of a handle of the endoscope, wherein movement of the second lever on the first lever from a first position to a second position disengages engagement of the lock sections.

A method of operating an endoscope can be provided comprising rotating a finger lever in a first direction from a first locked position to a second unlocked position, wherein the finger lever is pivotably connected to a control lever, and wherein the control lever is connected to a control wire pulley of a deflection control system of an endoscope; and after the finger lever is moved to the second unlocked position, moving the finger lever in a second direction to thereby rotate the control lever and control wire pulley in the second direction.

The method can further comprise, after the finger lever and control lever are rotated in the second direction to a user selected location, allowing a spring to pivot the finger lever on the control lever in a third direction opposite to the first direction such that a lock section of the finger lever engages a lock section on a handle of the endoscope.

One of the features of the invention is the spring loaded control lever subassembly. In the embodiment shown in the drawings, the subassembly comprises the two levers 34, 36, spring 48 and pin 46. One of the features of the invention is a locking/breaking assembly having the pin 46 on the lever 36 and the engaged pad 54 on the frame 30; which can be used with only one hand/finger operation. The engagement between the pin and pad can be (for example) frictional engagement, positive locking engagement (such as a pin being located into a hole), and/or a detent or ratchet type of relative position locating system.

Figure 10:
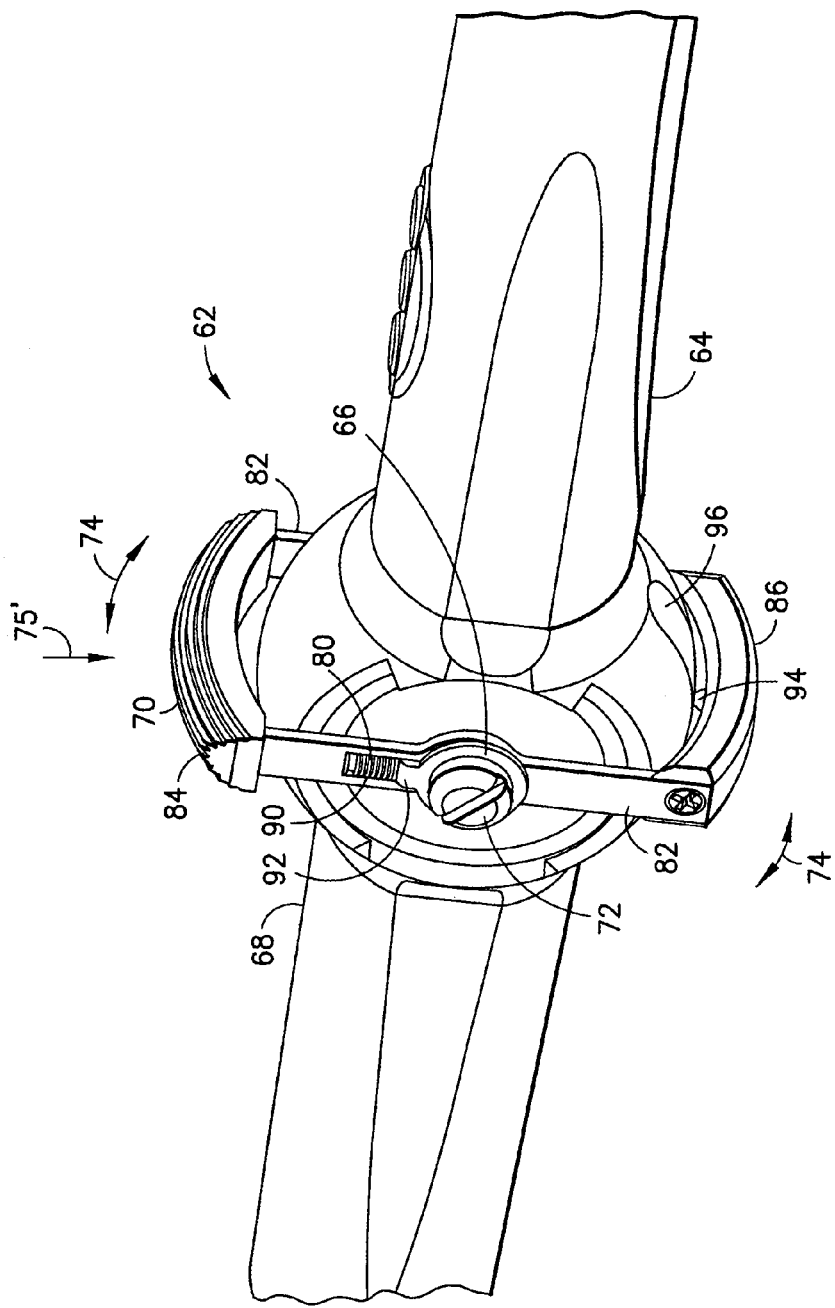
FIG. 10 is a partial perspective view of an alternate embodiment of she invention.

Referring now to FIG. 10, an alternate embodiment of the invention is shown. In this example embodiment rather than having the front distal end 16 which is configured to deflect horizontally left and right, the endoscope 62 has a front distal end which is configured to deflect vertically up and down. Rather than having the vertically orientated pulley 28, the main section 64 has a vertically orientated pulley with external ends 66 which are located at lateral sides of the frame 68. The pulley and deflection control wires extending up to the front distal end form part of a deflection control for a user to control deflection of the deflectable front end from the main section 14. The deflection control also comprises a lever assembly 70. The lever assembly 70 is connected to the external ends 66 of the pulley by screws 72 to axially rotate the pulley when the lever assembly 70 is rotated forward or backward as indicated by arrows 74 in FIG. 10.

Figure 11:
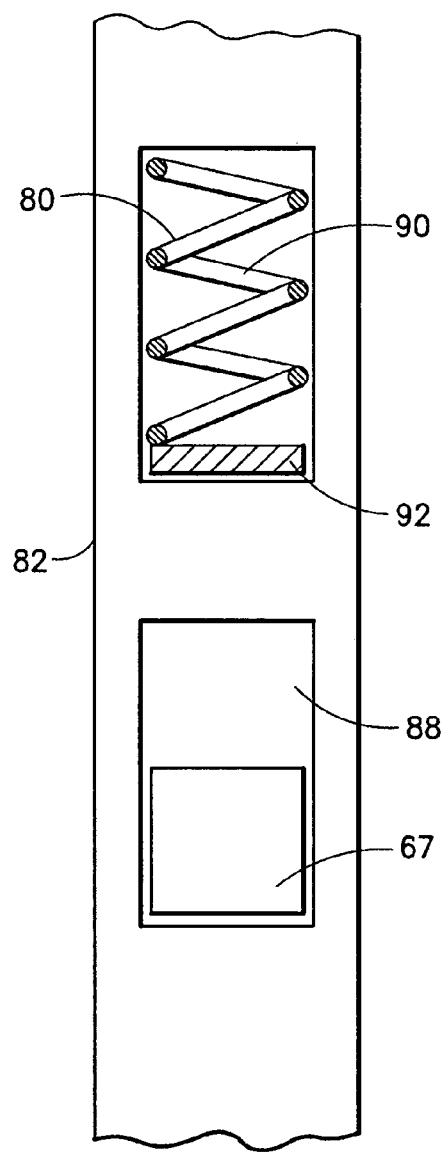
FIG. 11 is a cross sectional view of some of the components shown in FIG. 10.

The lever assembly 70 comprises a lever member 76 and a spring 80. The lever member 76 has two arms 82 located on opposite lateral sides of the frame 68. Top and bottom sections 84, 86 connect the two arms 82 to each other. As seen in FIG. 11, each arm 82 has an elongate slot 88 at its center. At least one of the arms 82 also has a spring receiving pocket 90. In this example embodiment, square end sections 67 of the pulley shafts are slidably located in the slots 88. A portion 92 of the external end 66 of the pulley is located in the pocket 90. The spring 80 is located in the pocket 90 and biases the portion 92 towards the bottom of the pocket 90. More specifically, the spring 80 biases the lever member 76 upward as indicated by arrow 75.

The bottom section 86 has a brake/lock pin 94. The frame 68 has a brake/lock pad or pin engaging area 96. When the lever member 76 is biased upward by the spring(s) 80, this biases the pin 94 into a brake or lock position with the pad 76 to prevent rotation of the lever member 76 and, thus, prevent rotation of the deflection control wire pulley. In order to actively deflect the front distal end of the shaft up or down, the user can push the top section 84 downward as indicated by arrow 75'. Slots 88 provide clearance for the arms 82 relative to the screws 72. The spring(s) 80 is compressed in pocket(s) 90. The user can then rotate the lever member 76 backward or forward as indicated by arrow 74. Once the desired deflection of the front distal end is obtained, the user can release the lever member 76, and the spring(s) 80 can bias the lever member back to an upward home position. The pin 94 engages the pad 96 again to lock or frictionally engage the lever assembly 70 with the frame 68 again and thereby retain the distal front end at its deflected configuration/position.

A single finger of a user can be used to unlock the locking engagement of the pin 94 and pad 96 (by pressing down 75' on top section 84), rotate the deflection control wire pulley with the same finger (by rotating the tops section 84 forward or backward), and re-engage the locking engagement of the pin 94 and pad 96 (by releasing the finger from the top section 84 and allowing the springs(80) to bias the lever member 76 back to it home position). The lever assembly 70 can provide a combined lock and deflection control member at the handle, wherein the lever assembly 70 (combined lock and deflection control member) is adapted to be moved to a selected location by a single finger of a user and thereby deflect the distal end, and wherein the control member is adapted to be locked at a user selected location by movement of the lever assembly 70 (combined lock and deflection control member) to a locked position by the single finger of the user (in this case the single finger releasing depression of the lever member 76).

Figure 12:
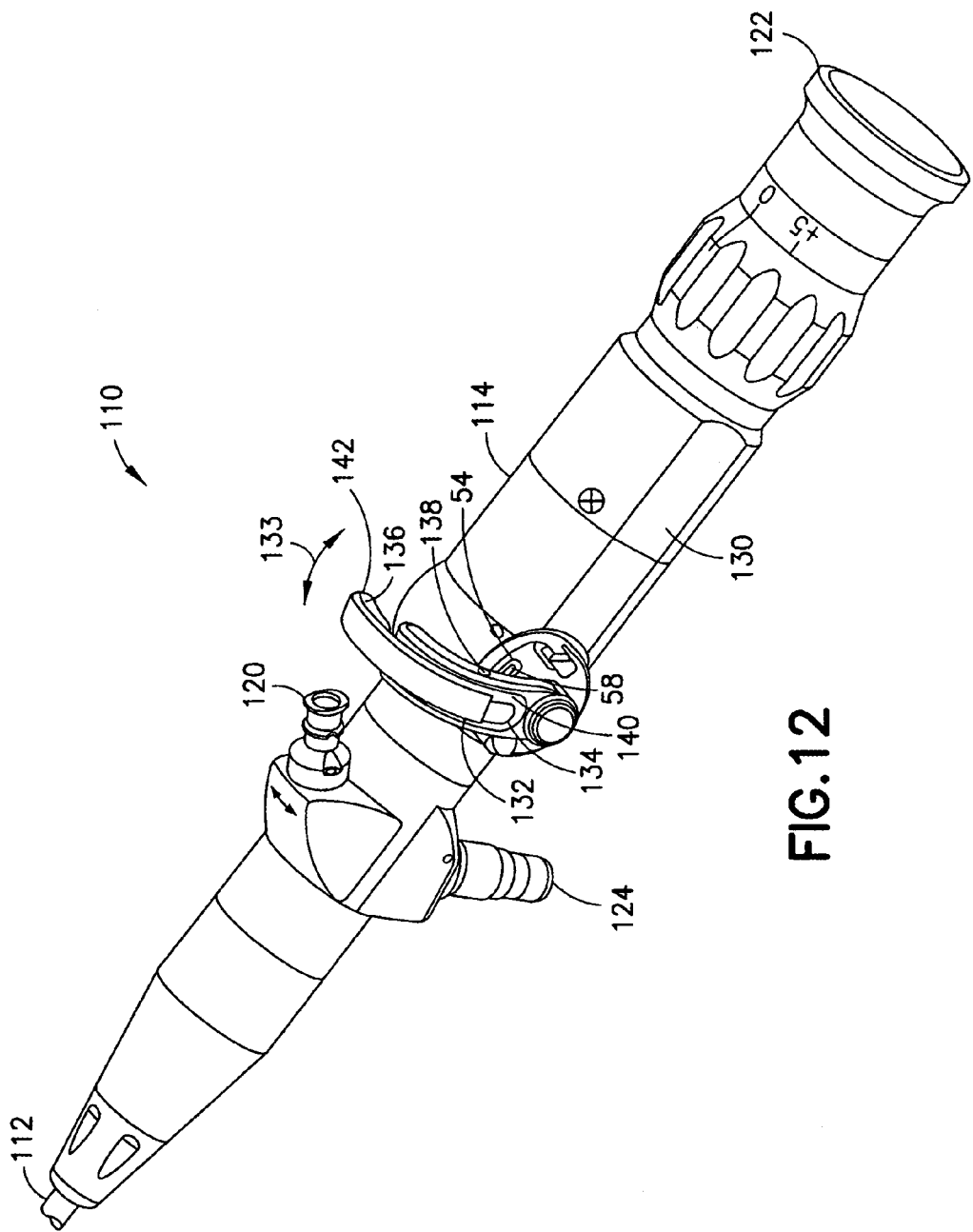
FIG. 12 is a perspective view of another example embodiment.

Referring also to FIG. 12, another example embodiment is shown. In this example the endoscope 110 comprises a shaft 112 and a main section 114 which forms a handle. The shaft 112 has a front or distal end which is controllably deflectable. The distal end is adapted to deflection in up and down directions. However, any suitable deflection capability could be provided.

The main section 114 is located at the proximal end of the shaft 112. The main section 114 has a working instrument/irrigation inlet 120, an eyepiece 122, and a fiber optics connector 124. Deflection control wires or cables extend from the distal end to a pulley in the main section 114. The pulley is rotatably mounted in the frame 130 of the main section 114.

The pulley and deflection control wires form part of a deflection control for a user to control deflection of the deflectable distal end from the main section 114. The deflection control also comprises a lever assembly 132. The lever assembly 132 is connected to the pulley to axially rotate the pulley when the lever assembly 132 is rotated forwards or backwards as indicated by arrows 133. The lever assembly 132 comprises a control lever 131 and a lock lever 136. The control lever 134 is fixedly connected to the pulley. The lock lever 136 is pivotably connected to the control lever 134 by a pivot 138. Thus, the lock lever 136 can pivot on the control lever 134, and the lock lever 136 is connected to the pulley by the control lever 134; in series. However, any suitable movable connection of the lock lever on the control lever could be provided.

The lock lever 136 has a first end 140 and a second end 142 on opposite sides of the pivot pin 138. The second end 142 forms a finger contact area. The first end 140 has a locking section on an inward facing side, such as a projection for example. In this embodiment the locking section is a pin attached to the first end 140. However, any suitable locking section could be provided. A spring is provided between the control lever and the lock lever to bias the second end 142 outward and the first end 140 inward on the control lever 134. However, a user can use his/her thumb to depress the second end 142 to thereby pivot the lock lever 136 at the pivot 138 and move the first end 140 outward.

The main section 114 includes a locking section or pad 54 located opposite the locking section of the lock lever 136. In this embodiment the pad 54 is an insert which is fixedly inserted into a receiving area of the main section. The insert has a general curved or arched shape. However, in an alternate embodiment the pad could be integrally formed with the frame of the main section, or any suitably sized and shaped locking section (for engaging with the locking section of the lock lever) could be provided. The pad 54 has a series of recesses 58. The recesses 58 are sized, shaped and arranged in an arch or curve to receive the bottom tip of the locking projection of the lock lever at different angular positions of the lever assembly 132. The recesses 58 allow positive location of the tip and, thus, positive location of the angular position of the lever assembly 32, at one of a plurality of fixed predetermined locations selected by the user. When the lock lever 136 is at its home position with the second end 142 biased outward by the spring, she tip is biased into one of the recesses 58. This prevents the lever assembly 132 from rotating relative to the main section 114 and, thus, prevents the lever assembly 132 from rotating the pulley. This forms a lock or brake for the deflection control system; fixing the position or shape of the distal end on the shaft 112. The projection from the first end 134 of the lock lever forms a first lock/brake section which engages with a second lock/brake section formed by the pad 54.

With the same hand holding the handle formed by the main section 114, the user can use his or her finger to depress the second end 142 of the lock lever 136 inward to thereby disengage the projection from the first end 140 of the lock lever from the lock pad 54. The user is then free to swing the lever assembly 132 (both levers 134, 136 moving together in unison) forward or backwards as indicated by arrows 133. Once a desired deflection of the distal end of the shaft is obtained, the user can release the second end 142 of the lock lever 136 and the spring can automatically biased the lock lever 136 back to its home position. This automatically locks the lever assembly at a fixed angular position on the main section 114 due to the re-engagement of the lock/brake sections on the lock lever first end and the main section.

In this example embodiment the endoscope main section is provided with a vertically oriented pulley, and the control/lock lever assembly rotates about the longitudinal axis of the endoscope main section. This assembly proximal portion is located on the upper side (or alternatively the lower side) of the endoscope main section. Multiple recesses may be provided on either side of the main section.

A single finger of a user can be used to unlock the locking engagement with the multiple recesses 58 by pushing the second end of the lock lever towards to the main section, and then rotating the deflection control wire pulley with the same finger by pushing the control/lock lever proximal section forward or backward. The locking engagement can then be re-engaged by-releasing the user finger from the control/lock lever proximal section.

Moving the control/lock lever assembly in this way enables more intuitive controls of the deflection at the distal tip of the flexible shaft of the endoscope. It may provide greater ease of use for the end user and can also be thought of as a change in design choice. For example, when the user desires to deflect the distal tip of the endoscope in an up/down configuration, it may be considered more intuitive if the lever is moved forward and backward.

When the user desires to deflect the distal tip of the endoscope from side to side, it may be considered more intuitive to move the lever left and right (see FIGS. 1-2). The way in which the control wires are connected from the distal tip of the flexible shaft of the endoscope into the control/lock lever assembly will ultimately determine how deflection occurs at the distal tip of the flexible shaft of the endoscope.

In one example, an endoscope comprises a shaft having a deflectable distal end; a main section at a proximal end of the shaft, where the main section forms a handle of the endoscope; and a deflection control connected no the distal end. The deflection control comprises a combined lock and deflection control member at one main section comprising a control lever pivotably connected to the main section at a pivot and extending away from the pivot in a general cantilever fashion, and a lock lever pivotably connected to the control lever. A first end of the lock lever is configured to contact the main section. A second end of the lock lever is configured to be pressed inward on the control lever by a user towards the main section to pivot the first end out of contact with the main section.

The combined lock and deflection control member may be adapted to be moved to a selected location by a single finger of a user and thereby deflect the distal end, wherein the combined lock and deflection control member is adapted to be locked at the user selected location by movement of the lock lever to a locked position by the single finger of the user. The control lever may be connected to a control wire pulley of the deflection control, wherein the control wire pulley is connected to the deflectable distal end. The lock lever may be biased by a spring on the control lever towards a locked position with the main section. The first end of the lock lever may comprise a projection adapted to contact a lock section on the main section when the lock lever is at a locked position, and wherein the projection is disengaged from the lock section on the main section when the lock lever is pivoted on the control lever to an unlocked position. The lock section on the main section may comprise a curved insert mounted onto the main section. The lock section on the main section may comprise recesses at predetermined locations along a curved path. A first section of the control lever may be located at a first exterior side of the main section and a second section of the control lever is located at an adjacent second exterior side of the handle, where the control lever has a cantilevered curved shape over the first and second exterior sides.

In another example, an endoscope comprises a shaft having a deflectable distal end; a handle at a proximal end of the shaft; and a deflection control connected to the distal end. The deflection control comprises a control lever pivotably connected to a first side of the handle, where the control lever extends from the first side of the handle in a general cantilever fashion, over an adjacent second side of the handle; and a lock lever pivotably connected to the control lever, wherein the lock lever comprises a lock section adapted to contact a lock section on the handle.

The control lever may be connected to a control wire pulley of the deflection control, wherein the control wire pulley is connected to the deflectable distal end by a control wire. The lock lever may be biased by a spring on the control lever towards a locked position with the handle. The lock lever may be pivotably connected to the control lever by a pivot, where the lock lever includes a first end and a second end on opposite sides of the pivot, where the first end comprises the lock section of the lock lever, where the second end comprises a finger contact area for a user to depress the second end and pivotably rotate the lock lever on the control lever, and wherein the lock section of the lock lever is disengaged from the lock section on the handle when the lock lever is moved on the control lever no an unlocked position. The lock section on she handle may comprise a curved insert mounted onto the handle. The lock section on the handle may comprise recesses at predetermined locations along a curved path. The control lever may have a longitudinally curved shape and the lock lever may have a longitudinally curved shape generally in a same direction of curvature as the control lever.

An example method may comprise pivotably connecting a control lever to a handle section of an endoscope, where the control lever is connected to a control wire pulley of a deflection control system of the endoscope, where the control lever is adapted to be rotated on the handle section to rotate the pulley; and pivotably connecting a lock lever to the control lever, where the lock lever is adapted to pivot on the control lever between a locked position and an unlocked position, where in the locked position a locking section on a first end of the lock lever engages a lock section of the handle section, and where in the unlocked position the locking section on the first end of the lock lever does not engage the lock section of the handle section. The method may further comprise locating a spring between the control lever and the lock lever to bias the lock lever towards the locked position.

Another example method may comprise rotating a lock lever in a first direction from a first locked position to a second unlocked position, where the lock lever is pivotably connected to a control lever, where the control lever is pivotably connected to a control wire pulley of a deflection control system of the endoscope; and after the lock lever is moved to the second unlocked position, moving the lock lever and the control lever together in a second different direction to thereby rotate the control wire pulley. The method may further comprise, after the lock lever and control lever are rotated in the second direction to a user selected location, allowing a spring to pivot the lock lever on the control lever in a third direction opposite to the first direction such that a lock section of the lock lever engages a lock section on a handle section of the endoscope.

It should be understood that the foregoing description is only illustrative of the invention. Various alternatives and modifications can be devised by those skilled in the art without departing from the invention. For example, features recited in the various dependent claims could be combined with each other in any suitable combination(s). In addition, features from different embodiments described above could be selectively combined into a new embodiment. Accordingly, the invention is intended to embrace all such alternatives, modifications and variances which fall within the scope of the appended claims.

What is claimed is:

1. An endoscope comprising:
   a shaft having a deflectable distal end;
   a main section at a proximal end of the shaft, where the main section forms a handle of the endoscope; and
   a deflection control connected to the distal end, wherein the deflection control comprises a combined lock and deflection control member at the main section comprising a control lever pivotably connected to the main section at a pivot and extending away from the pivot in a general cantilever fashion, and a lock lever pivotably connected to the control lever, where a first end of the lock lever is configured to contact the main section and where a second end of the lock lever is configured to be pressed inward on the control lever towards the main section to pivot the first end out of contact with the main section,
   wherein the first end of the lock lever comprises a projection adapted to contact a lock section on the main section when the lock lever is at a locked position, and wherein the projection is disengaged from the lock section on the main section when the lock lever is pivoted on the control lever to an unlocked position.

2. An endoscope as in claim 1 wherein the combined lock and deflection control member is adapted to be moved to a selected location by a single finger of a user and thereby deflect the distal end, and wherein the combined lock and deflection control member is adapted to be locked at the user selected location by movement of the lock lever to a locked position by the single finger of the user.

3. An endoscope as in claim 1 wherein the control lever is connected to a control wire pulley of the deflection control, wherein the control wire pulley is connected to the deflectable distal end.

4. An endoscope as in claim 1 wherein the lock lever is biased by a spring on the control lever towards a locked position with the main section.

5. An endoscope as in claim 1 wherein the lock section on the main section comprises a curved insert mounted onto the main section.

6. An endoscope as in claim 1 wherein the lock section on the main section comprises recesses at predetermined locations along a curved path.

7. An endoscope as in claim 1 wherein a first section of the control lever is located at a first exterior side of the main section and a second section of the control lever is located at an adjacent second exterior side of the handle, where the control lever has a cantilevered curved shape over the first and second exterior sides.

8. An endoscope comprising:
   a shaft having a deflectable distal end;
   a handle at a proximal end of the shaft; and
   a deflection control connected to the distal end, wherein the deflection control comprises:
      a control lever pivotably connected to a first side of the handle, where the control lever extends from the first side of the handle in a general cantilever fashion, over an adjacent second side of the handle; and
      a lock lever pivotably connected to the control lever, wherein the lock lever comprises a lock section adapted to contact a lock section on the handle,
   wherein the lock lever is pivotably connected to the control lever by a pivot, where the lock lever includes a first end and a second end on opposite sides of the pivot, where the first end comprises the lock section of the lock lever, where the second end comprises a finger contact area for a user to depress the second end and pivotably rotate the lock lever on the control lever, and wherein the lock section of the lock lever is disengaged from the lock section on the handle when the lock lever is moved on the control lever to an unlocked position.

9. An endoscope as in claim 8 wherein the control lever is connected to a control wire pulley of the deflection control, wherein the control wire pulley is connected to the deflectable distal end by a control wire.

10. An endoscope as in claim 8 wherein the lock lever is biased by a spring on the control lever towards a locked position with the handle.

11. An endoscope as in claim 8 wherein the lock section on the handle comprises a curved insert mounted onto the handle.

12. An endoscope as in claim 8 wherein the lock section on the handle comprises recesses at predetermined locations along a curved path.

13. An endoscope as in claim 8 where the control lever has a longitudinally curved shape and where the lock lever has a longitudinally curved shape generally in a same direction of curvature as the control lever.

14. A method comprising:
- rotating a lock lever in a first direction from a first locked position to a second unlocked position, where the lock lever is pivotably connected to a control lever by a pivot, where the control lever is pivotably connected to a control wire pulley of a deflection control system of the endoscope; and
- after the lock lever is moved to the second unlocked position, moving the lock lever and the control lever together in a second different direction to thereby rotate the control wire pulley.

15. A method as in claim 14 further comprising, after the lock lever and control lever are rotated in the second direction to a user selected location, allowing a spring to pivot the lock lever on the control lever in a third direction opposite to the first direction such that a lock section of the lock lever engages a lock section on a handle section of the endoscope.

* * * * *